United States Patent [19]

Wilson et al.

[11] Patent Number: 5,750,715
[45] Date of Patent: May 12, 1998

[54] BIS[(1,2-BENZISOTHIAZOL-3(2H)-YLIDENE 1,1-DIOXIDE)ACETATES] CHARGE-CONTROL AGENTS

[75] Inventors: John C. Wilson; Robert D. Fields, both of Rochester, N.Y.

[73] Assignee: Eastman Kodak Company, Rochester, N.Y.

[21] Appl. No.: 818,668

[22] Filed: Mar. 14, 1997

[51] Int. Cl.$^6$ .................................. C07D 417/12
[52] U.S. Cl. .................................................. 548/209
[58] Field of Search ...................................... 548/209

[56] References Cited

U.S. PATENT DOCUMENTS

| | | | |
|---|---|---|---|
| 5,358,814 | 10/1994 | Osterhoudt et al. | 430/106.6 |
| 5,358,815 | 10/1994 | Wilson et al. | 430/106.6 |
| 5,358,816 | 10/1994 | Wilson et al. | 430/106.6 |
| 5,358,817 | 10/1994 | Wilson et al. | 430/106.6 |
| 5,358,818 | 10/1994 | Wilson et al. | 430/106.6 |

*Primary Examiner*—Johann Richter
*Assistant Examiner*—Laura R. C. Lutz
*Attorney, Agent, or Firm*—John R. Everett

[57] ABSTRACT

Bis[(1,2-benzisothiazol-3(2H)-ylidene 1,1-dioxide)acetates] are disclosed. They have the general structure (I):

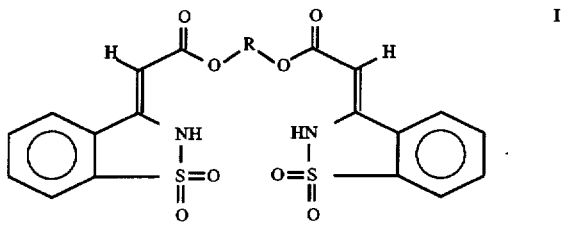

R is defined in the specification.

4 Claims, No Drawings

BIS[(1,2-BENZISOTHIAZOL-3(2H)-YLIDENE 1,1-DIOXIDE)ACETATES] CHARGE-CONTROL AGENTS

FIELD OF THE INVENTION

The present invention relates to electrostatographic developers and toners containing charge-control agents.

CROSS REFERENCE TO RELATED APPLICATIONS

The present application is related to the following titled applications, all in the name of Wilson and Fields and all filed on the same day as the present case:

1. U.S. Ser. No. 08/815,037 entitled Electrostatographic Toners and Developers Containing Bis[(1,2-benzisothiazol-3(2H)-ylidene 1,1-dioxide)acetates] Charge-Control Agents
2. U.S. Ser. No. 08/818,811 entitled Electrostatographic Toners and Developers containing Novel Bis[(1,2-benzisothiazol-3(2H)-ylidene 1,1-dioxide)acetates] Charge-Control Agents
3. U.S. Ser. No. 08/818,810 entitled Novel(1,2-Benzisothiazol-3-(2H)-ylidene 1,1-dioxide)acetate-terminated Polymer Charge-Control Agents for Electrostatographic Toners and Developers)
4. U.S. Ser. No. 08/816,096 entitled Electrostatographic Toners and Developers containing (1,2-Benzisothiazol-3-(2H)-ylidene 1,1-dioxide)acetate-terminated Polymer Charge-Control Agents

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

In electrostatography, the image charge pattern, also referred to as an electrostatic latent image, is formed on an insulative surface of an electrostatographic element by any of a variety of methods. For example, the electrostatic latent image may be formed electrophotographically, by imagewise photo-induced dissipation of the strength of portions of an electrostatic field of uniform strength previously formed on the surface of an electrophotographic element comprising a photoconductive layer and an electrically conductive substrate. Alternatively, the electrostatic latent image may be formed by direct electrical formation of an electrostatic field pattern on a surface of a dielectric material.

One well-known type of electrostatographic developer comprises a dry mixture of toner particles and carrier particles. Developers of this type are employed in cascade and magnetic brush electrostatographic development processes. The toner particles and carrier particles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in imagewise relation, to the latent image bearing surface. The resultant toner image can then be fixed, by application of heat or other known methods, depending upon the nature of the toner image and the surface, or can be transferred to another surface and then fixed.

Toner particles often include charge-control agents, which, desirably, provide high uniform net electrical charge to toner particles without reducing the adhesion of the toner to paper or other medium. Many types of positive charge-control agents, materials which impart a positive charge to toner particles in a developer, have been used and are described in the published patent literature. In contrast, few negative charge-control agents, materials which impart a negative charge to toner particles in a developer, are known.

Prior negative charge-control agents have a variety of shortcomings. Many charge-control agents are dark colored and cannot be readily used with pigmented toners, such as cyan, magenta, yellow, red, blue, and green. Some are highly toxic or produce highly toxic by-products. Some are highly sensitive to environmental conditions such as humidity. Some exhibit high throw-off or adverse triboelectric properties in some uses. Use of charge-control agents requires a balancing of shortcomings and desired characteristics to meet a particular situation.

SUMMARY OF THE INVENTION

The invention, in its broader aspects, provides a bis[(1,2-benzisothiazol-3(2H)-ylidene 1,1-dioxide)acetate] charge-control agent having the general structure (I):

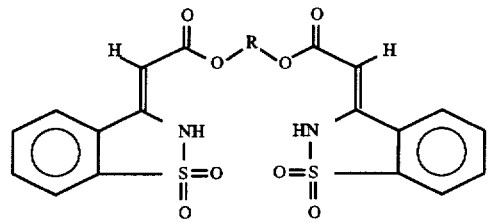

wherein R represents linear, branched or cyclic substituted or unsubstituted, $C_2$ to $C_{18}$ alkylene, such as ethylene, trimethylene, hexamethylene, 2,2-dimethyl-1,3-propanediyl, 1,4-cyclohexanedimethylene, 1,14-tetradecanediyl, 1,4-cyclohexanediyl, and the like; arylenedialkylene, such as, p-xylylene; alkylenediarylene, such as 4,4'-isopropylidenediphenylene, 4,4'-isopropylidenedi(2,6-dichlorophenylene), 1,1,3-trimethyl-3-(4-phenylene)indan-5-yl; bis(alkyleneoxyaryl)alkane, such as, 2,2-bis[4-(2-ethyleneoxy)phenyl]propane, 8,8-bis[4-(2-ethyleneoxy)phenyl]tricyclo[5.2.1.0 $^{2,6}$]decane; diphenylene with the general structure:

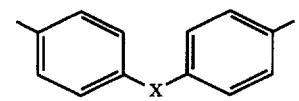

bis(alkyleneoxyaryl) with the general structure:

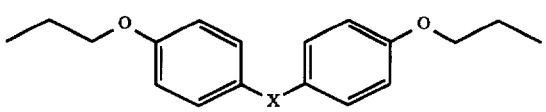

3

-continued where X = 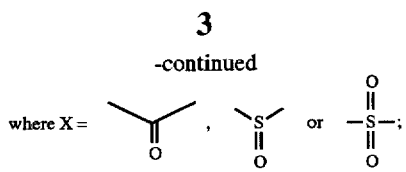

and arylene, such as 1,4-phenylene and 4,4'-biphenylene.

It is an advantageous effect of the invention that negatively charging toners can be provided which have favorable charging characteristics.

DETAILED DESCRIPTION

The term "particle size" as used herein, or the term "size," or "sized" as employed herein in reference to the term "particles," means the median volume weighted diameter as measured by conventional diameter measuring devices, such as a Coulter Multisizer, sold by Coulter, Inc. of Hialeah, Fla. Median volume weighted diameter is an equivalent weight spherical particle which represents the median for a sample; that is, half of the mass of the sample is composed of smaller particles, and half of the mass of the sample is composed of larger particles than the median volume weighted diameter.

The term "charge-control," as used herein, refers to a propensity of a toner addendum to modify the triboelectric charging properties of the resulting toner.

The term "glass transition temperature" or "$T_g$," as used herein, means the temperature at which a polymer changes from a glassy state to a rubbery state. This temperature ($T_g$) can be measured by differential thermal analysis as disclosed in "Techniques and Methods of Polymer Evaluation," Vol. 1, Marcel Dekker, Inc., New York, 1966.

The charge-control agents used in the present invention are prepared by condensing 3-cloro-1,2-benzisothiazole 1,1-dioxide with 2,2-dimethyl-1,3-dioxane-4,6-dione in methylene chloride in the presence of triethylamine to form 5-(1,2-benzisothiazol-3(2H)-ylidene 1,1-dioxide)-2,2-dimethyl-1,3-dioxane-4,6-dione; and heating the 5-(1,2-benzisothiazol-3(2H)-ylidene 1,1-dioxide) -2,2-dimethyl-1,3-dioxane-4,6-dione with glycols or bisphenols in refluxing toluene to form the bis[(1,2-benzisothiazol-3(2H)-ylidene 1,1-dioxide) acetates].

The chemical reaction path involved in this method of preparation is:

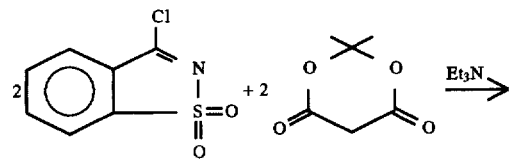

4

-continued

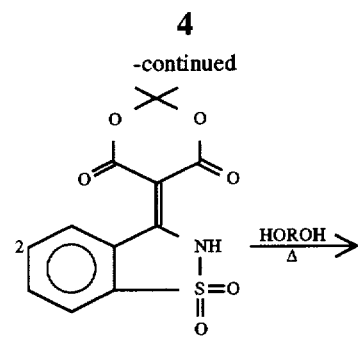

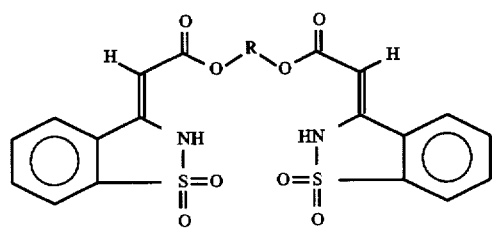

The bis[(1,2-benzisothiazol-3(2H)-ylidene 1,1-dioxide) acetates] can generally tautomerize. Thus, the general structure could, in many cases, also include the following tautomeric forms:

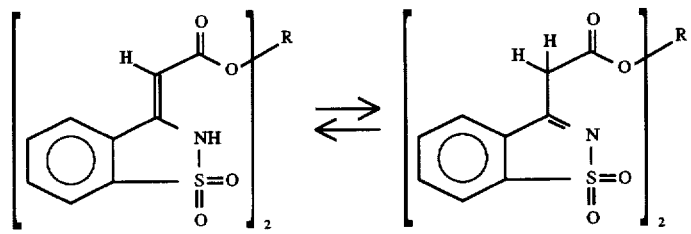

For the sake of brevity, alternate tautomeric forms will not be illustrated herein. However, structural formulas should be understood to be inclusive of alternate tautomers.

In addition to tautomeric forms, the compositions of the invention may, with respect to the 3-ylidene double bond, exist as geometric isomers. Although the configuration of the compounds of the invention are unknown, both geometric isomers are considered to fall within the scope of the invention.

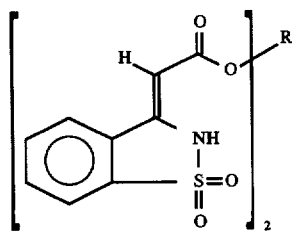

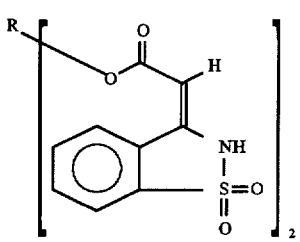

Both tautomeric forms and both geometric isomers may also be present in the same molecule.

The method of making the novel charge-control agents of the invention is illustrated in the following examples.

EXAMPLE 1

Step 1: Preparation of 5-(1,2-Benzisothiazol-3(2H)-ylidene 1,1-dioxide) -2,2-dimethyl-1,3-dioxane-4,6-dione

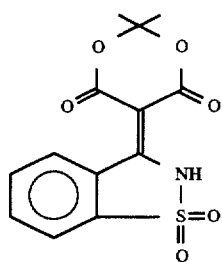

A solution of 100.82 g (0.50 mol) of 3-chloro-1,2-benzisothiazole 1,1-dioxide (prepared by the method of Stephen, et al., J. Chem. Soc., 1957, 490), 72.07 g (0.50 mol) of 2,2-dimethyl-1,3-dioxane-4,6-dione and 1 L of methylene chloride was prepared and cooled in an ice/water bath. To this solution was added 101.19 g (1.00 mol) of triethylamine dropwise over 35 min. The cooling bath was removed and the reaction mixture was stirred for 17.5 hrs, washed with 10% HCl and twice with water. The solution was dried over magnesium sulfate, filtered and concentrated. The residue was washed with warm ligroine and then with acetone. The yellow solid was recrystallized from 2-butanone, collected, washed with ligroine and dried.

Step 2: Preparation of 2,2-Bis[4-(2-hydroxyethoxy)phenyl]propane bis[(1,2-benzisothiazol-3(2H)-ylidene 1,1-dioxide)acetate]

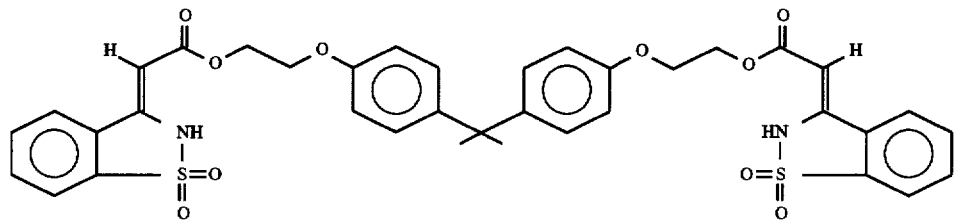

A mixture of 3.16 g (10 mmol) of 2,2-bis[4-(2-hydroxyethoxy)phenyl]propane, 6.19 g (20 mmol) of 5-(1,2-benzisothiazol-3(2H)-ylidene 1,1- dioxide)-2,2-dimethyl-1,3-dioxane-4,6-dione and 100 ml of toluene was heated at reflux for 30 min and cooled. Solid crystallized which was collected, washed with ligroine and dried. Recrystallization from acetonitrile gave the final product.

Some of the bis[(1,2-benzisothiazol-3(2H)-ylidene 1,1-dioxide)acetates] that can be prepared by the method of the invention are presented in Table 1.

TABLE 1

Bis[(1,2-benzisothiazol-3(2H)-ylidene 1,1-dioxide)acetates]

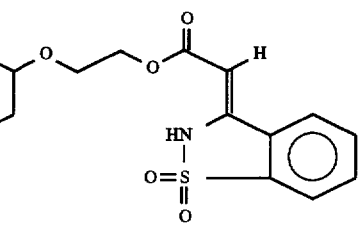

| Number | R |
| --- | --- |
| Example 1 | $-[(CH_2)_2O-p-C_6H_4]_2C(CH_3)_2$ |
| Example 2 | $-[(CH_2)_2O-p-C_6H_4]_2SO_2$ |
| Example 3 | $-[(CH_2)_2O-p-C_6H_4]_2R^{1*}$ |
| Example 4 | $-CH_2C(CH_3)_2CH_2-$ |
| Example 5 | $-[p-C_6H_4]_2C(CH_3)_2$ |

*$R^1$ represents

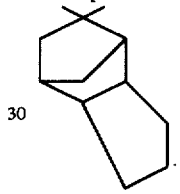

The charge-control agents of the invention also are essentially colorless and exhibit excellent thermal stability in air.

The toners provided by the invention include a charge-control agent of the invention, in an amount effective to modify, and improve the properties of the toner. It is preferred that a charge-control agent improve the charging characteristics of a toner, so the toner quickly charges to a negative value having a relatively large absolute magnitude and then maintains about the same level of charge. The compositions used in the toners are negative charge-control agents, thus the toners of the invention achieve and maintain negative charges.

It is also preferred that a charge-control agent improve the charge uniformity of a toner composition, that is, it insures that substantially all of the individual toner particles exhibit a triboelectric charge of the same sign with respect to a given carrier. It is also preferred that a charge-control agent be colorless, particularly for use in light colored toners. The charge-control agents of the invention are generally colorless. It is also preferred that a charge-control agent be metal free and have good thermal stability. The charge-control agents of the invention are metal free and have good thermal stability. Preferred materials described herein are based upon an evaluation in terms of a combination of characteristics rather than any single characteristic.

The binders used in formulating the toners of the invention with the charge-controlling additive of the present invention are polyesters having a glass transition temperature of 50° to 100° C. and a weight average molecular weight of 10,000 to 100,000. The polyesters are prepared from the reaction product of a wide variety of diols and dicarboxylic acids. Some specific examples of suitable diols are: 1,4-cyclohexanediol; 1,4-cyclohexanedimethanol; 1,4-cyclohexanediethanol; 1,4-bis(2-hydroxyethoxy)cyclohexane; 1,4-benzenedimethanol; 1,4-benzenediethanol; norbornylene glycol; decahydro-2,6-naphthalenedimethanol; bisphenol A; ethylene glycol; diethylene glycol; triethylene glycol; 1,2-propanediol, 1,3-propanediol; 1,4-butanediol; 2,3-butanediol; 1,5-pentanediol; neopentyl glycol; 1,6-hexanediol; 1,7-heptanediol; 1,8-octanediol; 1,9-nonanediol; 1,10-decanediol; 1,12-dodecanediol; 2,2,4-trimethyl-1,6-hexanediol; 4-oxa-2,6-heptanediol and etherified diphenols.

Suitable dicarboxylic acids include: succinic acid; sebacic acid; 2-methyladipic acid; diglycolic acid; thiodiglycolic acid; fumaric acid; adipic acid; glutaric acid; cyclohexane-1,3-dicarboxylic acid; cyclohexane-1,4-dicarboxylic acid; cyclopentane-1,3-dicarboxylic acid; 2,5-norbornanedicarboxylic acid; phthalic acid; isophthalic acid; terephthalic acid; 5-butylisophthalic acid; 2,6-naphthalenedicarboxylic acid; 1,4-naphthalenedicarboxylic acid; 1,5-naphthalenedicarobxylic acid; 4,4'-sulfonyldibenzoic acid; 4,4'-oxydibenzoic acid; binaphthyl-dicarboxylic acid; and lower alkyl esters of the acids mentioned.

Polyfunctional compounds having three or more carboxyl groups, and three or more hydroxyl groups are desirably employed to create branching in the polyester chain. Triols, tetraols, tricarboxylic acids, and functional equivalents, such as pentaerythritol, 1,3,5-trihydroxypentane, 1,5-dihydroxy-3-ethyl-3-(2-hydroxyethyl)pentane, trimethylolpropane, trimellitic anhydride, pyromellitic dianhydride, and the like are suitable branching agents. Presently preferred polyols are glycerol and trimethylolpropane. Preferably, up to about 15 mole percent, preferably 5 mole percent, of the reactant diol/polyol or diacid/polyacid monomers for producing the polyesters can be comprised of at least one polyol having a functionality greater than two or poly-acid having a functionality greater than two.

Variations in the relative amounts of each of the respective monomer reactants are possible for optimizing the physical properties of the polymer.

The polyesters of this invention are conveniently prepared by any of the known polycondensation techniques, e.g., solution polycondensation or catalyzed melt-phase polycondensation, for example, by the transesterification of dimethyl terephthalate, dimethyl glutarate, 1,2-propanediol and glycerol.

The polyesters also can be prepared by two-stage polyesterification procedures, such as those described in U.S. Pat. No. 4,140,644 and U.S. Pat. No. 4,217,400. The latter patent is particularly relevant, because it is directed to the control of branching in polyesterification. In such processes, the reactant glycols and dicarboxylic acids, are heated with a polyfunctional compound, such as a triol or tricarboxylic acid, and an esterification catalyst in an inert atmosphere at temperatures of 190° to 280° C., especially 200° to 240° C. Subsequently, a vacuum is applied, while the reaction mixture temperature is maintained at 220° to 240° C., to increase the product's molecular weight.

The degree of polyesterification can be monitored by measuring the inherent viscosity (I.V.) of samples periodically taken from the reaction mixture. The reaction conditions used to prepare the polyesters should be selected to achieve an I.V. of 0.10 to 0.80 measured in methylene chloride solution at a concentration of 0.25 grams of polymer per 100 milliliters of solution at 25° C. An I.V. of 0.10 to 0.60 is particularly desirable to insure that the polyester has a weight average molecular weight of 10,000 to 100,000, preferably 55,000 to 65,000, a branched structure and a Tg in the range of about 50° to about 100° C. Amorphous polyesters are particularly well suited for use in the present invention. After reaching the desired inherent viscosity, the polyester is isolated and cooled.

One useful class of polyesters comprises residues derived from the polyesterification of a polymerizable monomer composition comprising:
a dicarboxylic acid-derived component comprising:
about 75 to 100 mole % of dimethyl terephthalate and
about 0 to 25 mole % of dimethyl glutarate and
a diol/poly-derived component comprising
about 90 to 100 mole % of 1,2-propanediol and
about 0 to 10 mole % of glycerol.

Many of the afore described polyesters are disclosed in the patent to Alexandrovich et al, U.S. Pat. No. 5,156,937.

Another useful class of polyesters is the non-linear reaction product of a dicarboxylic acid and a polyol blend of etherified diphenols disclosed in U.S. Pat. Nos. 3,681,106; 3,709,684; and 3,787,526.

The etherified diphenols of U.S. Pat. No. 3,787,526 have the formula:

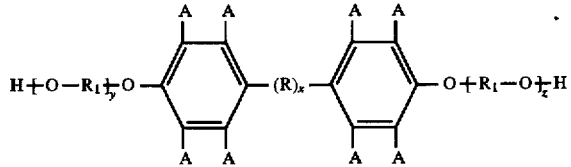

wherein z is 0 or 1;
R is an alkylene radical containing from 1 to 5 carbon atoms, a sulfur atom, an oxygen atom, or a radical characterized by the formula:

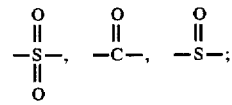

$R_1$ is an ethylene or propylene radical; x and y are integers with the proviso that the sum of x and y in said polyol blend is an average of from about 2.0 to about 7; and each A is individually selected from the group consisting of hydrogen and halogen atoms; and from about 0.01 to about 2.0 mol percent of an alkoxylated polyhydroxy compound, which polyhydroxy compound contains from 3 to 12 carbon atoms and from 3 to 9 hydroxyl groups and wherein the alkoxylated polyhydroxy compound contains from 1 to 10 mols of oxyalkylene groups per hydroxyl group of said polyhydroxy compound and said oxyalkylene radical is ethylene or propylene;
the number of carboxyl groups of said dicarboxylic acid to the number of hydroxyl groups of said polyol blend is in a ratio of from about 1.2 to about 0.8.

Among those diphenols which are contemplated as the base for the etherified diphenols used in the preparation of the polyesters are:

2,2-bis(1-hydroxyphenyl) propane;
bis(4-hydroxyphenyl) ethane;
3,3-bis(4-hydroxyphenyl) pentane;
p,p'-dihydroxydiphenol;
4,4'-dihydroxydiphenyl ether;
4,4'-dihydroxydiphenyl thioether;
4,4'-dihydroxydiphenyl ketone;
2,2'-bis(4-hydroxy-2,6-dichlorophenyl) propane;
2-fluoro-4-hydroxyphenyl sulfoxide;
4,4'-dihydroxydiphenyl sulfone;
2,3,6-dichlorobromo-4-hydroxyphenyl-2,6-dichloro-4-hydroxyphenyl methane; and
2,2-bis(2,3,5,6-tetrabromo-4-hydroxyphenyl)butane.

A preferred group of etherified bisphenols within the class characterized by the above formula in U.S. Pat. No. 3,787,526 are polyoxypropylene 2,2'-bis(4-hydroxyphenyl) propane and polyoxyethylene or polyoxypropylene, 2,2-bis(4-hydroxy, 2,6-dichlorophenyl) propane wherein the number of oxyalkylene units per mol of bisphenol is from 2.1 to 2.5.

The etherified diphenols disclosed in U.S. Pat. No. 3,709,684 are represented by the formula:

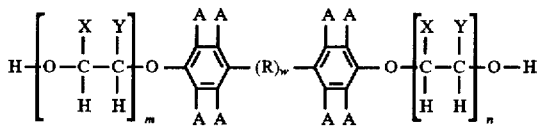

In this formula w represents an integer of 0 or 1; R is an alkylene radical of one to five carbon atoms, oxygen, sulfur or a divalent radical represented by the formula:

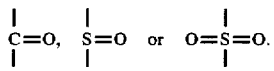

Each A is individually selected from either a halogen atom or a hydrogen atom; the letters m and n are integers from 0 through 6 with the proviso that the sum of m and n is at least about 2 and less than 7; and X and Y are radicals which are individually selected from the following group: alkyl radicals of one to three carbon atoms, a phenyl radical, or a hydrogen atom; provided that in any X and Y pair on adjacent carbon atoms either X or Y is a hydrogen atom. A preferred group of etherified diphenols within the above formula include those where each A is either a chlorine atom or hydrogen and/or R is an alkylene radical containing one to three carbon atoms, and X and Y are either hydrogen or a methyl radical. In this preferred group the average sum of n and m is at most about 3. Examples of etherified diphenols within the above formula include the following: polyoxyethylene(3)-2,2-bis(4-hydroxyphenyl) propane; polyoxystyrene(6)-bis(2,6-dibromo-4-hydroxyphenyl) methane; polyoxybutylene(2.5)-bis(4-hydroxyphenyl) ketone; polyoxyethylene(3)-bis(4-hydroxphenyl) ether; polyoxystyrene(2.8)-bis(2,6-dibromo-4-hydroxyphenyl) thioether; polyoxypropylene(3)bis(4-hydroxyphenyl) sulfone; polyoxystyrene(2)-bis(2,6-dichloro-4-hydroxyphenyl) ethane; polyoxyethylene(3)-bis(4-hydroxyphenyl) thioether; polyoxy-propylene(4)-4,4'-bisphenol; polyoxyethylene(7)-bis(2,3,6-trifluorodichloro-4-hydroxyphenyl) ether; polyoxyethylene(3,5)-4,4-bis(4-hydroxyphenyl) pentane; polyoxystyrene(4)-2-fluoro-4-hydroxyphenyl, 4-hydroxyphenyl sulfoxide; and polyoxybutylene(2)-3,2-bis (2,3,6-tribromo-4-hydroxyphenyl) butane.

A class of readily available etherified diphenols within the above formula from U.S. Pat. No. 3,709,684 are the bisphe-
nols. A preferred class of etherified bisphenols are those prepared from 2,2-bis(4-hydroxy-phenyl) propane or the corresponding 2,6,2',6'-tetrachloro or tetrafluoro bisphenol alkoxylated with from 2 to 4 mols of propylene or ethylene oxide per mol of bisphenol.

The etherified diphenols disclosed in U.S. Pat. No. 3,681,106 have the formula:

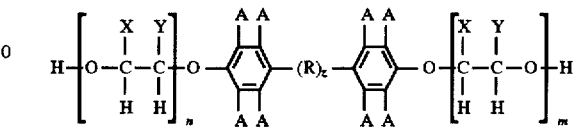

wherein z is 0 or 1, R is an alkylene radical containing from 1 to 5 carbon atoms, a sulfur atom, an oxygen atom,

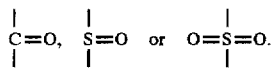

X and Y are individually selected from the group consisting of alkyl radicals containing from 1 to 3 carbon atoms, hydrogen, and a phenyl radical with the limitation that at least X or Y is hydrogen in any X and Y pair on adjacent carbon atoms, n and m are integers with the proviso that the average sum of n and m is from about 2 to about 7; and each A is either a halogen atom or a hydrogen atom. An average sum of n and m means that in any polyol blend some of the etherified diphenols within the above formula may have more than 7 repeating ether units but that the average value for the sum of n and m in any polyhydroxy composition is from 2 to 7. Examples of compounds within the above general formula from U.S. Pat. No. 3,681,106 are:

polyoxystyrene(6)-2,2-bis(4-hydroxyphenyl) propane;
polyhydroxybutylene(2)-2,2-bis(4-hydroxyphenyl) propane;
polyoxyethylene(3)-2,2-bis(4-hydroxyphenyl) propane;
polyoxypropylene(3)-bis(4-hydroxyphenyl) thioether;
polyoxyethylene(2)-2,6-dichloro-4-hydroxyphenyl, 2',3',6'-trichloro-4'-hydroxyphenyl methane;
polyoxypropylene(3)-2-bromo-4-hydroxyphenyl, 4'-hydroxyphenyl ether;
polyoxyethylene(2.5)-p,p-bisphenol;
polyoxybutylene(4)-bis(4-hydroxyphenyl) ketone;
polyoxystyrene(7)-bis(4-hydroxyphenyl) ether;
polyoxypentylene(3)-bis(2,6-difluoro-4-hydroxyphenyl) propane; and
polyoxypropylene(2.2)-2,2-bis(4-hydroxyphenyl) propane.

A preferred group of said etherified diphenols are those where the average sum of n and m is from about 2 to about 3. Thus, although the sum of n and m in a given molecule may be as high as about 20, the average sum in the polyol composition will be about 2 to about 3. Examples of these preferred etherified diphenols include:

polyoxyethylene(2.7)-4-hydroxyphenyl-2-chloro-4-hydroxyphenyl ethane;
polyoxyethylene(2.5)-bis(2,6-dibromo-4-hydroxyphenyl) sulfone;
polyoxypropylene(3)-2,2-bis(2,6-difluoro-4-hydroxyphenyl) propane; and
polyoxyethylene(1.5)-polyoxypropylene(1.0)-bis(4-hydroxyphenyl) sulfone.

A preferred polyhydroxy composition used in said polyester resins are those polyhydroxy compositions containing up to 2 mol percent of an etherified polyhydroxy compound, which polyhydroxy compound contains from 3 to 12 carbon atoms and from 3 to 8 hydroxyl groups. Exemplary of these polyhydroxy compounds are sugar alcohols, sugar alcohol anhydrides, and mono and disaccharides. A preferred group of said polyhydroxy compounds are sorbitol, 1,2,3,6-hexantetrol; 1,4-sorbitan; pentaerythritol, xylitol, sucrose, 1,2,4-butanetriol, 1,2,5-pentanetriol; xylitol; sucrose, 1,2,4-butanetriol; and erythro and threo 1,2,3-butanetriol. Said etherified polyhydroxy compounds are propylene oxide or ethylene oxide derivatives of said polyhydroxy compounds containing up to about 10 molecules of oxide per hydroxyl group of said polyhydroxy compound and preferably at least one molecule of oxide per hydroxyl group. More preferably the molecules of oxide per hydroxyl group is from 1 to 1.5. Oxide mixtures can readily be used. Examples of these derivatives include polyoxyethylene(20) pentaerythritol, polyoxypropylene(6) sorbitol, polyoxyethylene(65) sucrose, and polyoxypropylene(25) 1,4-sorbitan. The polyester resins prepared from this preferred polyhydroxy composition are more abrasion resistant and usually have a lower liquid point than other crosslinked polyesters herein disclosed.

Polyesters that are the non-linear reaction product of a dicarboxylic acid and a polyol blend of etherified polyhydroxy compounds, discussed above, are commercially available from Reichold Chemical Company. To illustrate the invention the examples provided herein use an poly (etherified bisphenol A fumarate) sold as Atlac 382ES by Reichold.

An optional but preferred component of the toners of the invention is colorant: a pigment or dye. Suitable dyes and pigments are disclosed, for example, in U.S. Pat. No. Re. 31,072 and in U.S. Pat. Nos. 4,160,644; 4,416,965; 4,414, 152; and 2,229,513. One particularly useful colorant for toners to be used in black and white electrostatographic copying machines and printers is carbon black. Colorants are generally employed in the range of from about 1 to about 30 weight percent on a total toner powder weight basis, and preferably in the range of about 2 to about 15 weight percent.

The toners of the invention can also contain other additives of the type used in previous toners, including leveling agents, surfactants, stabilizers, and the like. The total quantity of such additives can vary. A present preference is to employ not more than about 10 weight percent of such additives on a total toner powder composition weight basis.

The toners can optionally incorporate a small quantity of low surface energy material, as described in U.S. Pat. Nos. 4,517,272 and 4,758,491. Optionally the toner can contain a particulate additive on its surface such as the particulate additive disclosed in U.S. Pat. No. 5,192,637.

A performed mechanical blend of particulate polymer particles, charge-control agent, colorants and additives can, alternatively, be roll milled or extruded at a temperature sufficient to melt blend the polymer or mixture of polymers to achieve a uniformly blended composition. The resulting material, after cooling, can be ground and classified, if desired, to achieve a desired toner powder size and size distribution. For a polymer having a "$T_g$" in the range of about 50° C. to about 120° C., a melt blending temperature in the range of about 90° C. to about 150° C. is suitable using a roll mill or extruder. Melt blending times, that is, the exposure period for melt blending at elevated temperature, are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification can be accomplished using one or two steps.

In place of blending, the polymer can be dissolved in a solvent in which the charge-control agent and other additives are also dissolved or are dispersed. The resulting solution can be spray dried to produce particulate toner powders. Limited coalescence polymer suspension procedures as disclosed in U.S. Pat. No. 4,833,060 are particularly useful for producing small sized, uniform toner particles.

The toner particles have an average diameter between about 0.1 micrometers and about 100 micrometers, and desirably have an average diameter in the range of from about 1.0 micrometer to 30 micrometers for currently used electrostatographic processes. The size of the toner particles is believed to be relatively unimportant from the standpoint of the present invention; rather the exact size and size distribution is influenced by the end use application intended. So far as is now known, the toner particles can be used in all known electrostatographic copying processes.

The amount of charge-control agent used typically is in the range of about 0.2 to 10.0 parts per hundred parts of the binder polymer. In particularly useful embodiments, the charge-control agent is present in the range of about 1.0 to 4.0 parts per hundred.

The developers of the invention include carriers and toners of the invention. Carriers can be conductive, non-conductive, magnetic, or non-magnetic. Carriers are particulate and can be glass beads; crystals of inorganic salts such as ammonium chloride, or sodium nitrate; granules of zirconia, silicon, or silica; particles of hard resin such as poly(methyl methacrylate); and particles of elemental metal or alloy or oxide such as iron, steel, nickel, carborundum, cobalt, oxidized iron and mixtures of such materials. Examples of carriers are disclosed in U.S. Pat. Nos. 3,850, 663 and 3,970,571. Especially useful in magnetic brush development procedures are iron particles such as porous iron, particles having oxidized surfaces, steel particles, and other "hard" and "soft" ferromagnetic materials such as gamma ferric oxides or ferrites of barium, strontium, lead, magnesium, copper, zinc or aluminum. Copper-zinc ferrite powder is used as a carrier in the examples hereafter. Such carriers are disclosed in U.S. Pat. Nos. 4,042,518; 4,478, 925; and 4,546,060.

Carrier particles can be uncoated or can be coated with a thin layer of a film-forming resin to establish the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Polymeric silane coatings can aid the developer to meet the electrostatic force requirements mentioned above by shifting the carrier particles to a position in the triboelectric series different from that of the uncoated carrier core material to adjust the degree of triboelectric charging of both the carrier and toner particles. The polymeric silane coatings can also reduce the frictional characteristics of the carrier particles in order to improve developer flow properties; reduce the surface hardness of the carrier particles to reduce carrier particle breakage and abrasion on the photoconductor and other components; reduce the tendency of toner particles or other materials to undesirably permanently adhere to carrier particles; and alter electrical resistance of the carrier particles.

In a particular embodiment, the developer of the invention contains from about 1 to about 20 percent by weight of toner of the invention and from about 80 to about 99 percent by weight of carrier particles. Usually, carrier particles are larger than toner particles. Conventional carrier particles have a particle size of from about 5 to about 1200 micrometers and are generally from 20 to 200 micrometers.

The toners of the invention are not limited to developers which have carrier and toner, and can be used, without carrier, as single component developer.

The toner and developer of the invention can be used in a variety of ways to develop electrostatic charge patterns or latent images. Such developable charge patterns can be prepared by a number of methods and are then carried by a suitable element. The charge pattern can be carried, for example, on a light sensitive photoconductive element or a non-light-sensitive dielectric surface element, such as an insulator coated conductive sheet. One suitable development technique involves cascading developer across the electrostatic charge pattern. Another technique involves applying toner particles from a magnetic brush. This technique involves the use of magnetically attractable carrier cores. After imagewise deposition of the toner particles the image can be fixed, for example, by heating the toner to cause it to fuse to the substrate carrying the toner. If desired, the unfused image can be transferred to a receiver such as a blank sheet of copy paper and then fused to form a permanent image.

The invention is further illustrated by the following Examples.

PREPARATION OF TONERS

A poly(etherified bisphenol A fumarate) was heated and melted on a 4 inch two roll melt compounding mill. The polyester base polymer was Atlac 382ES manufactured by Reichold Chemical. One roll was heated and controlled to a temperature of 120° C., the other roll was cooled with chilled water. After melting the polyester, the charge-control agent and any pigments were added to the melt. A typical batch formula was 50 g of polyester and 0.5 g of charge-control agent, giving a product with 1 part charge-control agent per 100 parts of polymer. The melt was compounded for 20 minutes, peeled from the mill and cooled. The melt was then coarse ground to approximately 2 mM in a laboratory mechanical mill and then fine ground in a Trost TX air jet mill. The ground toner had a mean particle size of approximately 8.5 µm.

Clear toners (toners containing only charge-control agent and polyester) were made for each charge-control agent example. A control toner containing no charge-control agent was made by the same compounding and grinding procedure.

Black and magenta toners, with and without (control) charge-control agents, were made using the same technique.

Black toners were made using Cabot Regal 300 carbon black added to the polymer melt while roll milling. Carbon black concentrations were 5 parts carbon per 100 parts of polyester.

Magenta toners were made by adding a magenta pigment to the melt while melt compounding. Pigment Red 122 (PR 122) (Sun Chemical) was used. Pigments were used in the concentration of 10 parts pigment/100 parts polymer.

PREPARATION OF DEVELOPERS

Developers (toners and carrier particles) were made for each prepared toner composition, including control toners. The carrier was a copper-zinc ferrite powder with a particle size of approximately 60 µm. The ferrite particles were coated with a polysilane. The carrier was made by Powdertech Corporation. Developers were made by blending 20 g of carrier and 0.8 g of toner. The toner concentration was 4 parts toner per 100 parts carrier.

SURFACE TREATMENT

Developers containing black or magenta pigmented toners are frequently surface treated with silica to improve their powder flow properties. Accordingly developers, containing black or magenta toners and carriers, were surface treated by adding amorphous silica powder to the carrier and toner blend. The silica had a specific BET surface area of 110 $m^2/g$. Degussa R972 silica was used for surface treatment. For each surface treated developer, 0.004 g of silica was added to a mixture of 0.8 g of toner and 20 g of carrier to give a silica concentration of 0.5 parts per 100 parts of toner.

MEASUREMENT OF TONER CHARGE

The various developers were separately exercised by shaking a vial containing 20 g of developer on a wrist shaker with an amplitude of approximately 11 cm and frequency of 120 Hz. The developer was shaken and samples taken after 2, 10, 60, and 120 minutes of exercising.

A weighed sample (about 0.15 g) of the exercised developer was placed on a 50 micron mesh wire screen. Toner was removed by passing a vacuum tube containing a fine mesh filter across the backside of the screen. The tube was brass and insulated from the screen by a plastic tip. The brass tube body was connected to an electrometer that measured the total charge in microcoulombs on the toner collected by the filter. After all the toner was removed from the carrier the total charge was recorded and the filter containing toner removed and weighed. The charge to mass ratio (Q/m) of the toner was calculated by dividing the total charge by the toner weight to give Q/m in microcoulombs per gram (µc/g).

Results of these measurements for clear, black and magenta toners are presented hereafter in Tables 2.

EVALUATION OF CHARGING PROPERTIES

Effective charge-control agents are ones that increase the absolute charge level of the toner relative to the control toner containing no charge-control agent. The level of charge can generally be increased by increasing the concentration of the charge-control agent.

Surface treatment of toner with fine silica improves the image quality of prints made with it, and also effects the triboelectric properties of the toner. Silica surface treatment has the effect of raising the absolute initial charge/mass level of a toner. The charge level of a black surface treated toner containing no charge-control agent measured at 2 and 10 minutes is significantly higher than the same formulation with no surface treatment. Surface treatment has little to no effect on the Q/m of toners after 60 and 120 minutes exercise time.

Effective charge-control agent in silica surface treated toners raises the Q/m of toners that have been exercised 60 and 120 minutes. Such toners will give more consistent print densities and image quality in electrophotographic printers.

Toners that charge rapidly and maintain that charge with extended exercise time are desirable. The initial Q/m indicates if the toner is charging rapidly. Measurements at 60 and 120 minutes indicate whether the material is maintaining a constant charge with life. This exercise time represents the mixing that the developer experiences in a electrophotographic printer.

Exercised toners that show a little or no decrease in Q/m over time are preferred over formulations that show a large decrease. A toner with a constant charge level will maintain a consistent print density when compared to a formulation that does not have a constant charge/mass level.

Table 2 establishes that the bis[(1,2-benzisothiazol-3(2H)-ylidene 1,1-dioxide)acetates] are effective charge-control agents for clear, black and color toners.

TABLE 2

Bis[(1,2-benzisothiazol-3(2H)-ylidene 1,1-dioxide)acetates]
Charge-Control Properties

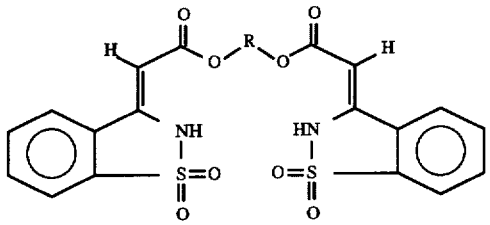

I

| Charge-control agent | R | pph | 2 min | 10 min | 60 min | 120 min |
|---|---|---|---|---|---|---|
| | | | | —Q/m | | |
| CLEAR TONER | | | | | | |
| Control | | 0.00 | 36.2 | 38.9 | 39.7 | 40.0 |
| Example 1 | —[(CH$_2$)$_2$O-p-C$_6$H$_4$]$_2$C(CH$_3$)$_2$ | 0.25 | 32.4 | 38.9 | 45.0 | 43.8 |
| | | 1.00 | 31.2 | 36.0 | 43.2 | 43.1 |
| Example 2 | —[(CH$_2$)$_2$O-p-C$_6$H$_4$]$_2$SO$_2$ | 0.25 | 39.5 | 39.5 | 44.3 | 40.6 |
| | | 1.00 | 39.8 | 40.7 | 49.2 | 47.1 |
| Example 3 | —[(CH$_2$)$_2$O-p-C$_6$H$_4$]$_2$R$^{1a}$ | 0.25 | 36.6 | 36.8 | 45.2 | 40.3 |
| | | 1.00 | 39.3 | 38.5 | 45.3 | 42.1 |
| Example 4 | —CH$_2$C(CH$_3$)$_2$CH$_2$— | 0.25 | 31.0 | 33.2 | 41.6 | 40.6 |
| | | 1.00 | 32.7 | 35.3 | 45.1 | 43.2 |
| Example 5 | -[p-C$_6$H$_4$]$_2$C(CH$_3$)$_2$ | 1.0 | 34.2 | 37.5 | 43.0 | 42.6 |
| | | 4.0 | 40.6 | 47.3 | 52.5 | 53.5 |
| BLACK TONER WITH SILICA | | | | | | |
| Control | | 0.00 | 29.8 | 28.8 | 22.8 | 16.3 |
| Example 1 | —[(CH$_2$)$_2$O-p-C$_6$H$_4$]$_2$C(CH$_3$)$_2$ | 1.0 | 28.8 | 27.1 | 22.8 | 21.2 |
| | | 4.0 | 28.8 | 28.4 | 24.0 | 20.3 |
| MAGENTA (PR 122) TONER WITH SILICA | | | | | | |
| Control | | 0.00 | 46.3 | 39.4 | 31.2 | 26.9 |
| Example 1 | —[(CH$_2$)$_2$O-p-C$_6$H$_4$]$_2$C(CH$_3$)$_2$ | 1.0 | 42.9 | 43.0 | 33.4 | 32.2 |
| | | 4.0 | 50.9 | 42.3 | 36.5 | 32.1 | a, R$^1$ =

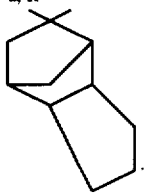

While specific embodiments of the invention have been shown and described herein for purposes of illustration, the protection afforded by any patent which may issue upon this application is not strictly limited to a disclosed embodiment; but rather extends to modifications and arrangements which fall fairly within the scope of the claims which are appended hereto.

It is claimed:

1. A bis[(1,2-benzisothiazol-3(2H)-ylidene 1,1-dioxide) acetate] having the general structure (I):

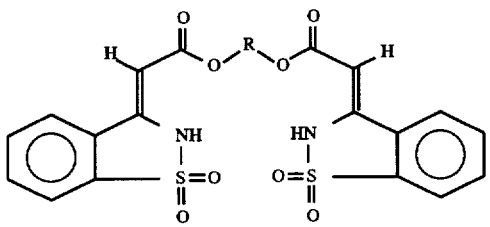

wherein R represents C$_2$ to C$_{18}$ alkylene; arylenedialkylene; alkylenediarylene; bis(alkyleneoxyaryl)alkane; diphenylene; bis(alkyleneoxyaryl); and arylene.

2. A bis[(1,2-benzisothiazol-3(2H)-ylidene 1,1-dioxide) acetate] according to claim 1 wherein R represents ethylene, trimethylene, hexamethylene, 2,2-dimethyl-1,3-propanediyl, 1,4-cyclohexanedimethylene, 1,14-tetradecanediyl, 1,4-cyclohexanediyl, p-xylylene, 4,4'-isopropylidenediphenylene, 4,4'-iso-propylidenedi(2,6-dichlorophenylene), 2,2-bis[4-(2-ethyleneoxy)phenyl]propane, 8,8-bis[4-(2-ethyleneoxy)phenyl]tricyclo[5.2.1.0 $^{2,6}$]decane, diphenylene with the general structure:

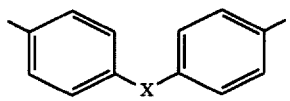

wherein X = 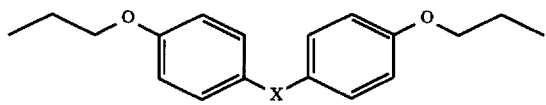

bis(alkyleneoxyaryl) with the general structure:

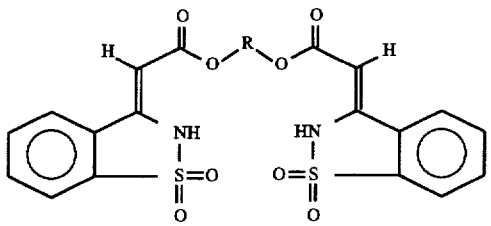

1,4-phenylene and 4,4'-biphenylene.

3. A bis[(1,2-benzisothiazol-3(2H)-ylidene 1,1-dioxide) acetate] according to claim 1 wherein R represents —CH$_2$C(CH$_3$)$_2$ CH$_2$—, —[(CH$_2$)$_2$O—p—C$_6$H$_4$]$_2$SO$_2$, —[(CH$_2$)$_2$O—p—C$_6$H$_4$]$_2$C(CH$_3$)$_2$, —[p—C$_6$H$_4$]$_2$C(CH$_3$)$_2$, or —[(CH$_2$)$_2$O—p—C$_6$H$_4$]$_2$R$^1$ in which R$^1$ represents:

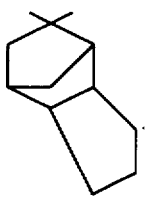

4. A method of preparing bis[(1,2-benzisothiazol-3(2H)-ylidene 1,1-dioxide)acetates] having the general structure:

wherein R represents C$_2$ to C$_{18}$ alkylene; arylenedialkylene; alkylenediarylene; bis(alkyleneoxyaryl)alkane; diphenylene; bis(alkyleneoxyaryl); and arylene, comprising the steps of:

condensing 3-chloro-1,2-benzisothiazole 1,1-dioxide with 2,2-dimethyl-1,3-dioxane-4,6-dione in methylene chloride in the presence of triethylamine to form 5-(1,2-benzisothiazol-3(2H)-ylidene 1,1-dioxide)-2,2-dimethyl-1,3-dioxane-4,6-dione; and heating the 5-(1,2-benzisothiazol-3(2H)-ylidene 1,1-dioxide)-2,2-dimethyl-1,3-dioxane-4,6-dione with glycols or bisphenols in refluxing toluene to form the bis[(1,2-benzisothiazol-3(2H)-ylidene 1,1-dioxide) acetates].

* * * * *